United States Patent [19]
Ishihara et al.

[11] Patent Number: 6,061,583
[45] Date of Patent: May 9, 2000

[54] NONINVASIVE BLOOD ANALYZER

[75] Inventors: Ken Ishihara, Takarazuka; Kaoru Asano, Kobe; Yasuhiro Kouchi, Kobe; Hideo Kusuzawa, Kobe, all of Japan

[73] Assignee: Sysmex Corporation and Ken Ishihara, Hyogo, Japan

[21] Appl. No.: 09/077,743

[22] PCT Filed: Dec. 27, 1996

[86] PCT No.: PCT/JP96/03894

§ 371 Date: Jun. 11, 1998

§ 102(e) Date: Jun. 11, 1998

[87] PCT Pub. No.: WO97/24066

PCT Pub. Date: Jul. 10, 1997

[30] Foreign Application Priority Data

Dec. 27, 1995 [JP] Japan ................................. 7-352971
May 15, 1996 [JP] Japan ................................. 8-146577

[51] Int. Cl.[7] ................................................ A61B 5/00
[52] U.S. Cl. ........................ 600/322; 600/473; 600/476
[58] Field of Search ................................. 600/310, 322, 600/473, 476, 479; 356/39

[56] References Cited

U.S. PATENT DOCUMENTS 4,998,533  3/1991  Winkelman .
5,372,136  12/1994  Steuer et al. .
5,722,398  3/1998  Ishihara et al. ....................... 600/322

FOREIGN PATENT DOCUMENTS 0712602     5/1996   European Pat. Off. .
63-206655   8/1988   Japan .
2239844     9/1990   Japan .
B2 3-71135  11/1991  Japan .
556982      3/1993   Japan .
6165784     6/1994   Japan .
7308311     11/1995  Japan .
7308312     11/1995  Japan .
9313706     7/1993   WIPO .

*Primary Examiner*—Eric F. Winakur

[57] ABSTRACT

A noninvasive blood analyzer is provided which comprises: a light source for illuminating a part of tissues of a living body including a blood vessel; an image pickup section for picking up an image of the illuminated blood vessel and tissues; and an analyzing section for analyzing the picked image; the analyzing section including an extracting section for extracting image density distribution across the blood vessel in the image as an image density profile, a quantifying section for quantifying configurational characteristics of the image density profile, a computing section for computing the concentration of a blood constituent on the basis of the quantified characteristics, and an outputting section for outputting a computation result. The blood analyzer can measure the concentration of blood hemoglobin and the hematocrit in real time with an improved repeatability without blood sampling.

23 Claims, 13 Drawing Sheets

NONINVASIVE BLOOD ANALYZER

This application is the national phase under 35 U.S.C. 0371 of prior PCT International Application No. PCT/JP96/03894 which has an International filing date of Dec. 27, 1996 which designated the United States of America, the entire contents of which are hereby incorporated by reference.

DESCRIPTION

1. Technical Field

The present invention relates to a noninvasive blood analyzer. The analyzer of the present invention is capable of transcutaneously monitoring an amount of a blood constituent such as hemoglobin concentration or hematcrit in real time with an improved repeatability without sampling blood from a living body.

2. Background Art

The hematology test of blood in a peripheral blood vessel is one of the most important and frequently performed tests in the clinical examination. Particularly, test items essential for the diagnosis on the case of anemia are hemoglobin concentration and hematocrit. The hematology test currently performed requires blood sampling from patients. However, the frequent blood sampling imposes a burden on patients and creates a risk of infection due to accidental sticking with an injection needle.

In view of the foregoing, there have been proposed apparatuses for transcutaneous (noninvasive) measurement on the aforesaid test items. For example, Japanese Examined Patent Publication No. HEI- 3-71135 discloses a hemoglobin concentration measurement apparatus for measuring blood hemoglobin on the basis of a change in the light intensity due to pulsation of light of a plurality of wavelengths projected onto a living body. Similarly, U.S. Pat. No. 5,372,136 discloses a system and method for determining hematocrit in blood by utilizing pulsation and the like.

However, a problem associated with the accuracy accompanies these arts for determining an absolute value, because the volume of the blood to be a test subject is not determined. Further, it is predicted that the measurements may vary depending on the body part to which the sensor is attached, resulting in a poor repeatability.

U.S. Pat. No. 4,998,533 discloses an apparatus for performing measurement on the aforesaid test categories on the basis of an image of a blood stream in blood capillary, which however, requires a large-scale construction. Although it has been reported that a transmitted light image of blood vessels in a part of a living body such as a finger can be obtained, no attempt has been made to perform a quantitative analysis on the aforesaid test items by analyzing the transmitted light image.

DISCLOSURE OF THE INVENTION

In view of the foregoing, the present invention provides an apparatus and method which are adapted to obtain a transmitted light image of a blood vessel in tissues of a living body such as a finger and analyze the transmitted light image with a simplified construction for performing measurement on the aforesaid test items with an improved repeatability.

More specifically, when light is allowed to pass through body tissues including a blood vessel and a transmitted light image is picked up, a blood vessel portion of the image is dark because of light absorption by blood constituent contained in blood, and the other image portion is bright because the other part of the body tissues transmits the light. In accordance with the present invention, the concentration of a blood constituent (e.g., hemoglobin) is quantified by a comparison of image densities and, when required, the determined concentration is corrected on the basis of the depth at which the blood vessel is present.

In accordance with the present invention, there is provided a noninvasive blood analyzer which comprises: a light source for illuminating a part of tissues of a living body including a blood vessel; an image pickup section for picking up an image of the illuminated blood vessel and tissues; and an analyzing section for analyzing the picked image; the analyzing section analyzing image density of the blood vessel in the picked image to compute an amount of a blood constituent and output a compution result.

In the present invention, the living body is meant by mammals including human, and the part of the tissues of the living body is meant by a part of tissues as they are in the living body, e.g., a finger or earlobe, but not meant by tissues separated from the living body.

In the analyzer of the present invention, the analyzing section may include an extracting section for extracting image density distribution across the blood vessel in the picked image as an image density profile, a quantifying section for quantifying configurational characteristics of the image density profile, a computing section for computing the amount of the blood constituent on the basis of the quantified characteristics, and an outputting section for outputting a computation result.

The analyzer of the present invention preferably further includes a fixing member for fixing the light source and the image pickup section relative to the part of the living body to allow the image pickup section to pick up an image of a desired portion of the tissues of the living body.

In the present invention, the picked image may be either a transmitted light image or a reflected light image.

Usable as the light source in the present invention are a semiconductor laser (hereinafter referred to as "LD"), an LED and a halogen light source. The part of the living body may be illuminated with the light directly or via an optical fiber. The wavelength of the light is preferably within a range between 400 and 950 nm, at which the light passes through the body tissues and the light absorption by water is not great. For example, a range between 600 and 950 nm is used for the transmitted light image while a range between 400 and 950 nm is used for the reflected light image.

More preferably, the light source is preferably comprised of a light emitting device which is adapted to selectively emit light beams of first and second wavelengths or light beams of three or more wavelengths. It is desirable that the first and second wavelengths are substantially isosbestic for oxidized and reduced hemoglobins.

Two or more wavelengths are required for the determination of an amount of a blood constituent, that is, hemoglobin concentration and hematocrit. If it is simply desired to monitor anemia condition, only one wavelength may be used.

The image pickup section may be comprised of an optical system including a lens and an image pickup device such as a CCD.

Since the image pickup section is simply adapted to take an image density profile across the blood vessel, a line sensor or a photodiode array may be used as the image pickup device instead of the CCD. The image density profile is preferably taken along a line perpendicular to the blood vessel.

Alternatively, the image density profile may be taken by moving a single photodiode in a direction across the blood vessel.

The optical system of the image pickup section can be constructed with a TV lens (e.g., BD1214D available from COSMICAR Inc.) alone.

Alternatively, the optical system of the image pickup section may be comprised of a pair of lenses having the same numerical aperture or the same focal distance and effective lens diameter, the pair of lenses respectively serving as an object lens and a focusing lens which are disposed along the same optical axis such that the front focal point of one lens coincides with the rear focal point of the other lens, and between which an optical space filter having two-dimensionally different transmittances is disposed (such an optical system is hereinafter referred to as "conjugate optical system"). The space filter herein used has a variation in the two-dimensional transmittance distribution. Usable as the space filter are a light blocking plate having a pin hole or an annular slit, and a liquid crystal shutter designed such that the transmittance distribution thereof can be changed by an electric signal.

The analyzing section includes the extracting section, the quantifying section, the computing section and the outputting section, and is adapted to compute on the basis of the obtained image density profile for determination of the amount of a blood constituent such as hemoglobin concentration, hematocrit or anemia condition and output the computation result. Usable for the analyzing section is a commercially available personal computer.

The extracting section of the analyzing section extracts image density distribution across the blood vessel as an image density profile from the picked image.

The quantifying section may normalize the extracted image density profile and compute a peak value h of the normalized image density profile.

Further, the quantifying section may determine a distribution width w corresponding to the diameter of the blood vessel in the image density profile and correct the peak value h on the basis of the distribution width w.

Where images of the same part of the tissues of the living body are picked up at the first and second wavelengths to afford first and second profiles respectively having peak values h1 and h2 and distribution widths w1 and w2, the quantifying section estimates the subcutaneous depth L of the blood vessel on the basis of the ratio between the distribution widths w1 and w2, and corrects the peak values h1 and h2. Thus, the computing section can compute the hemoglobin concentration and the hematocrit on the basis of the corrected peak values.

Where the conjugate optical system employs a light blocking plate having an annular slit as the space filter, the incident angle of light from the body tissues to the object lens is determined by the configuration (diameter or slit width) of the annular slit so that only the light entering at a predetermined incident angle serves to form a scatter light image of the blood vessel. The scatter light image reflects an influence of the disturbance of a blood vessel image by the body tissues. Therefore, by picking up scatter light images at a plurality of different scattering angles by changing the diameter of the annular slit, the quantifying section can quantify the influence of the body tissues to correct the detected concentration of the blood constituent more accurately.

In this case, since the scatter light image varies sensitively depending on the condition of the focusing on the blood vessel, the in-focus position can distinctly be detected by scanning the focal point of the image pickup section (object lens) from the surface of the body tissue to a deeper position, thereby allowing the quantifying section to directly determine the depth at which the blood vessel is present. Therefore, the aforesaid computation data can be corrected on the basis of the depth thus determined.

More specifically, a series of scatter light images of the blood vessel are obtained at a predetermined light incident angle by moving the focal point from the surface of the body tissues to the deeper position. Then, the quantifying section directly determines the depth L of the blood vessel on the basis of the position of the focal point at which the sharpest one of the series of the scatter light images is obtained, and the peak values h1 and h2 are corrected on the basis of the depth L.

Further, the quantifying section determines scatter absorption characteristics of the body tissues on the basis of a plurality of different scatter light images obtained at that focal point position by two-dimensionally varying the transmittance of the optical filter, and then corrects the peak values h1 and h2 and the distribution widths w1 and w2 on the basis of the scatter absorption characteristics.

The computing section computes the amount of the blood constituent such as hemoglobin concentration and hematocrit on the basis of the quantified configurational characteristics of the image density profiles. Here, hematocrit means a volume ratio of erythrocytes to blood. Usable as the outputting section are a CRT, an LCD and the like.

In accordance with another aspect of the present invention, there is provided a noninvasive blood analyzing process which comprises the steps of: illuminating a part of tissues of a living body including a blood vessel; picking up an image of the illuminated body tissues; and analyzing the picked image; the analyzing step including the steps of extracting image density distribution across the blood vessel in the picked image as an image density profile, quantifying configurational characteristics of the image density profile, computing an amount of a blood constituent on the basis of the quantified characteristics, and outputting a computation result.

Also, in accordance with the present invention, it can provide the noninvasive blood analyzing process further comprising the steps of: allowing an optical system to receive light from the body tissues at a predetermined incident angle with respect to an optical axis of the optical system and obtaining a series of scatter light images of the blood vessel by moving a focal point of the optical system from the surface of the body tissues to a deeper position; detecting the depth of the blood vessel on the basis of the position of the focal point at which the sharpest one of the series of the scatter light images is obtained; determining scatter/absorption characteristics of the body tissues on the basis of a plurality of scatter light images obtained at that focal point position by changing the incident light angle; and correcting the characteristics of the profile on the basis of the scatter/absorption characteristics.

BEST MODE FOR CARRYING OUT THE INVENTION

The present invention will hereinafter be described in detail by way of three embodiments. It should be noted that these embodiments are not limitative of the invention.

Embodiment 1

There will first be described the construction of a blood analyzer according to Embodiment 1 of the present invention.

Figure 1:
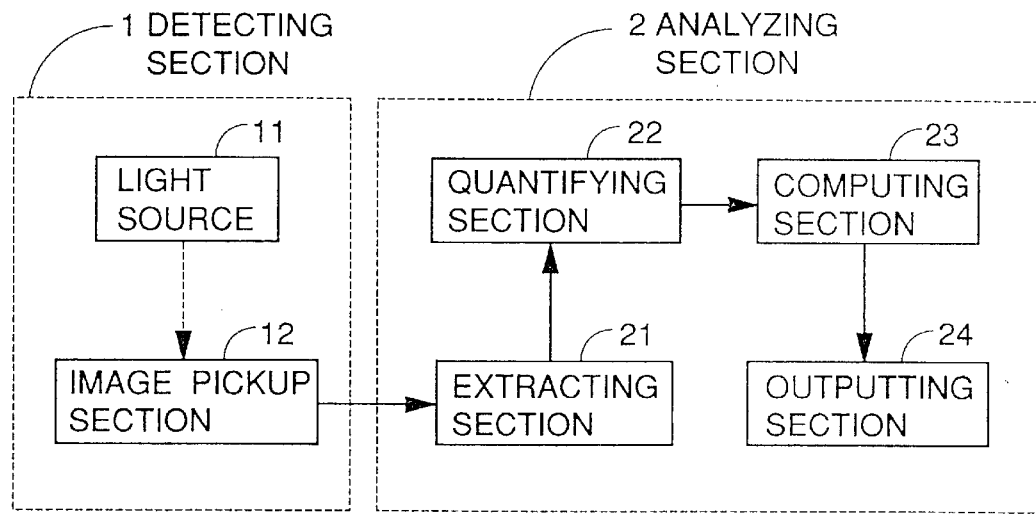
FIG. 1 is a block diagram illustrating the construction of a blood analyzer according to Embodiment 1 of the present invention.

FIG. 1 is a block diagram illustrating the construction of the blood analyzer. As shown, in a detecting section 1, it includes a light source 11 for illuminating a part of tissues of a living body including a blood vessel and an image pickup section 12 for picking up a transmitted light image of the illuminated blood vessel and tissues.

An analyzing section 2 includes an extracting section 21 for extracting image density distribution taken along a line perpendicular to the blood vessel in the image picked by the image pickup section 12 as an image density profile, a quantifying section 22 for quantifying the configurational characteristics of the extracted image density profile, a computing section 23 for computing the amount of a blood constituent on the basis of the quantified characteristics, and an outputting section (CRT) 24 for outputting a computation result. The analyzing section 2 may be comprised of a personal computer.

Figure 2:
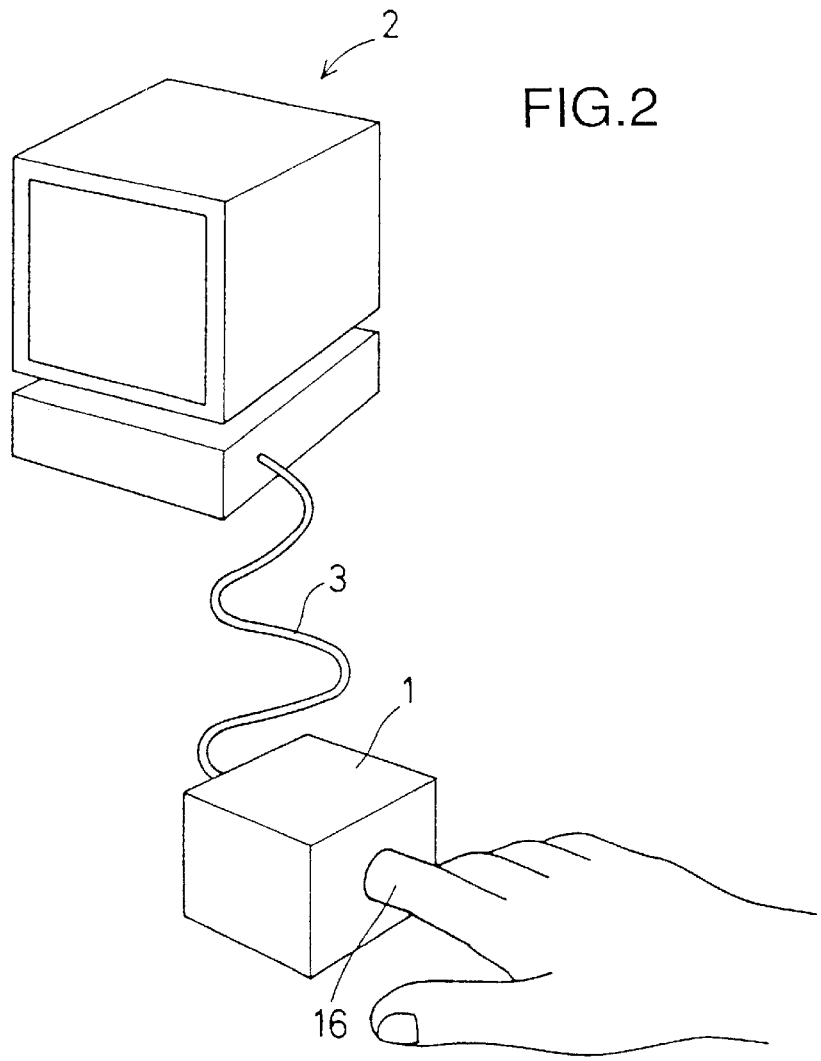
FIG. 2 is a perspective view illustrating the appearance of the blood analyzer of Embodiment 1 of the present invention.

FIG. 2 is a perspective view of the analyzer shown in FIG. 1. The light source 11 and the image pickup section 12 incorporated in the detecting section 1 are connected to the analyzing section 2 through signal cables 3.

Figure 3:
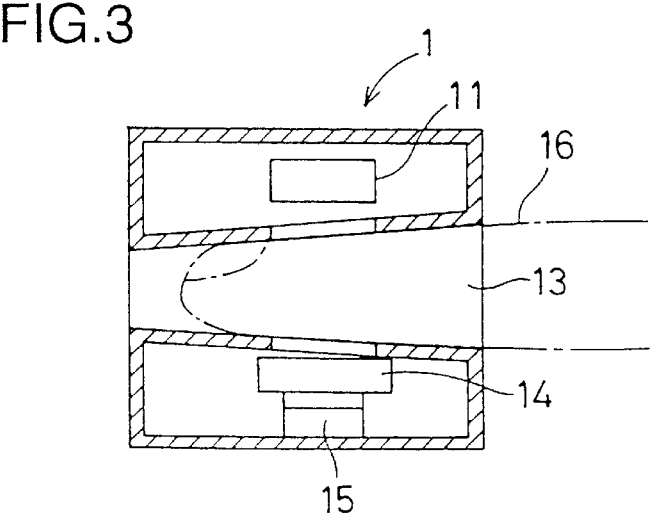
FIG. 3 is a sectional view illustrating a major portion of the blood analyzer of Embodiment 1 of the present invention.

FIG. 3 is a sectional view of the detecting section 1. The detecting section 1 includes the light source 11, and the image pickup section 12 having a lens 14 and an image pickup device 15. When a finger 16 is inserted into an open cavity 13, the light source 11 illuminates the finger 16 and an transmitted light image is picked up by the image pickup device 15 via the lens 14. The open cavity 13 gradually decreases toward the innermost position at which the finger tip is located, so that the inserted finger 16 is loosely fitted therein, thereby constituting a fixing member.

Figure 8:
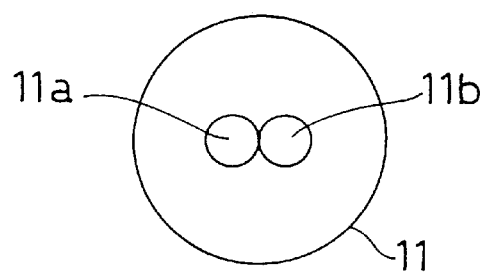
FIG. 8 is a front view of a light source of the blood analyzer of Embodiment 1 of the present invention.

The image pickup device 15 is comprised of a CCD. FIG. 8 is a front view of the light source 11, which includes LEDs 11a and 11b.

In this embodiment, the LED 11a employs VSF665M1 (available from OPTRANS Co.) having a center wavelength of 660 nm and a half value width 40 nm and the LED 11b employs L2656 (available from Hamamatsu Photonics Co.) having a center wavelength of 890 nm and a half value width 50 nm.

An analyzing process to be performed by the analyzing section 2 of the blood analyzer having such a construction will be described with reference to a flow chart shown in FIG. 4.

(1) Computation of Hemoglobin Concentration and Hematocrit

Figure 5:
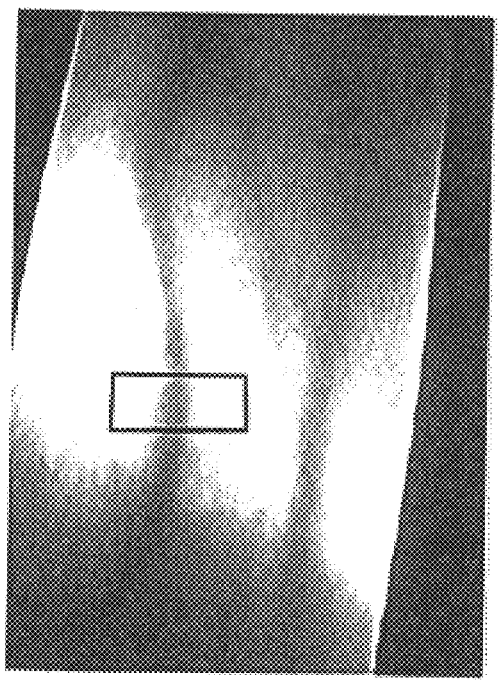
FIG. 5 is a photograph of an image (a gray scale image displayed on a CRT) picked by the blood analyzer of Embodiment 1 of the present invention.

When the finger is illuminated at a wavelength offered by the LED 11a (hereinafter be referred as "first wavelength") (Step 1) and a transmitted light image is picked up, an image of a blood vessel (vein) located near the skin on the side of the CCD 15 is obtained as shown in FIG. 5. Where the blood vessel of interest has a diameter of about 1 mm, quantitative results can be obtained with an improved repeatability.

In this case, where a highly coherent LD is used as the light source, an image free from speckles as shown in FIG. 5 can be obtained because the light is scattered by the tissues. In turn, an area in the image where the blood vessel stands in the sharpest contrast is searched for (Step 1a), and enclosed in a quadrilateral configuration as shown in FIG. 5, which is employed as an analytic area (Step 2).

Thus, a blood vessel at substantially a constant subcutaneous depth can be analyzed.

An image density profile (FIG. 6) along a line perpendicular to the blood vessel in this area is obtained (Step 3).

Figure 6:
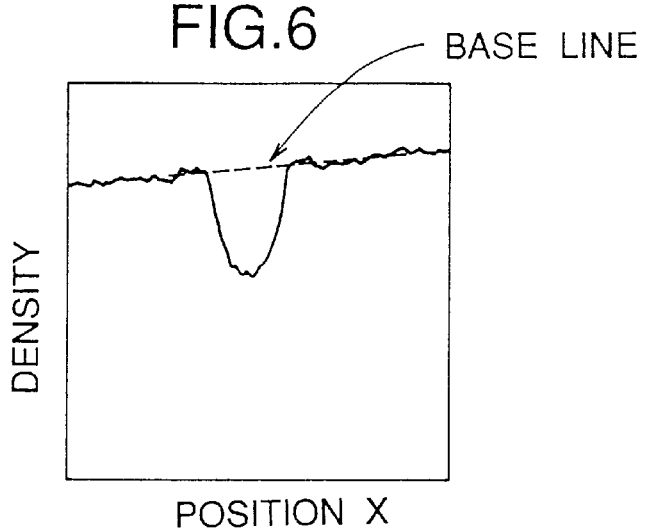
FIG. 6 is a graphical representation for explaining an image density profile obtained by the blood analyzer of Embodiment 1 of the present invention.
Figure 7:
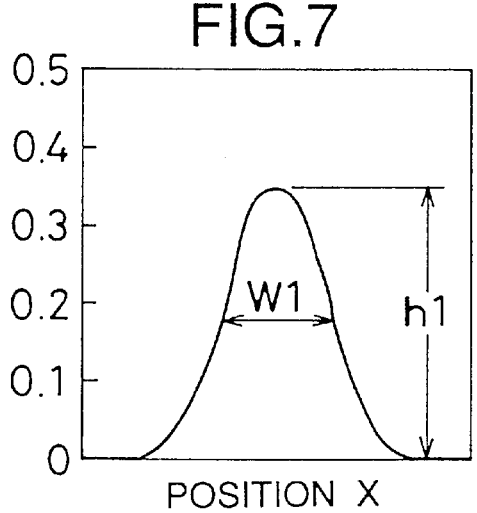
FIG. 7 is a graphical representation for explaining an image density profile normalized in the blood analyzer of Embodiment 1 of the present invention.

Then, the image density profile is normalized by a base line. The base line is determined on the basis of a portion of the image density profile corresponding to the tissues other than the blood vessel by the least square method. Thus, the image density profile of FIG. 6 is normalized as shown in FIG. 7 (Step 4).

The image density profile thus obtained is independent of the amount of incident light. A peak height h1 and a half value width (distribution width at a height of (½)h1) w1 are determined from the normalized image density profile (FIG. 7)(Step 5).

The peak height h1 thus obtained is indicative of the ratio of the image density of the blood vessel (i.e., a portion where blood is present) to the image density of the other portion where blood is absent. The parameter corresponding to a parameter which is obtained by the avascularization method (which is adapted to analyze blood on the basis of the ratio of the image density obtained when the blood is present to the image density obtained when the blood is avascularized) or by the pulsatile spectrometry (which is adapted to obtain signal components in synchronization with the pulsation of a blood flow and extract a signal component indicative of the pulsated blood flow for blood analysis, i.e., on the basis of the principle of a pulse oximeter) can be determined without the utilization of the pulsation or the avascularization.

More specifically, the scatter factor S1 and absorption factor factor A1 of the blood at the first wavelength, if conforming to the Beer Law, is expressed as follows:

$$\log(1-h1) = -k(S1+A1)w1 \quad (1)$$

wherein k is a proportional constant.

It is considered that the scatter factor S1 and the absorption A1 are directly proportional to the hematocrit HCT and the hemoglobin concentration HGB as follows:

$$S1 = \sigma1 \bullet HCT, \; A1 = \sigma2 \bullet HGB \quad (2)$$

Therefore, $$\log(1-h1) = -(k\sigma1 \bullet HCT + k\sigma2 \bullet HGB) \bullet w1 \quad (3)$$

The aforesaid process sequence is performed by employing a wavelength offered by the LED 11b (hereinafter referred to as "second wavelength") for determination of a peak height h2 and a distribution width w2 (Steps 6 to 10).

Similarly, the scatter factor S2 and the absorption factor A2 are determined as follows:

$$\log(1-h2) = -k(S2+A2) \bullet w2 = -(k\sigma3 \bullet HCT + k\sigma4 \bullet HGB) \bullet w2 \quad (4)$$

Since the constants k, σ1, σ2, σ3 and σ4 are experimentally determined, the HGB and the HCT are determined by h1, h2, w1 and w2.

In reality, the image is blurred by tissues intervening between the blood vessel and the detecting section and, hence, the observed peak values are smaller than the case where there are no intervening tissues. Therefore, the relation of the aforesaid factors are expressed as follows:

$$\log(1-h) = -k(S+A)w + T \quad (5)$$

wherein S is the scatter factor of the blood, A is the absorption factor of the blood, and T is a factor which indicates the influence of the blurring and is a function of the thickness L of the tissues (or the depth at which the blood vessel is located; hereinafter referred to simply as "depth").

It has been experimentally found that the factor T can be kept virtually constant by properly selecting a measuring area such that the blood vessel image in the obtained image stands in the sharpest contrast. Therefore, no practical problem arises if the factor T is regarded as a constant for application to an anemia checker.

(2) Correction of Computed Hemoglobin Concentration and Hematocrit

To improve the accuracy of the computation of the hemoglobin concentration and the hematocrit, the correction is made as follows.

When the analytic area is defined in the same area as defined by using the first wavelength, the half value widths w1 and w2 are equal to each other if the influence of the blurring is negligible. However, a difference between the half value widths w1 and w2 increases as the influence of the blurring increases (the half value width increases with the increase in the degree of the blurring).

Therefore, the depth L can be determined on the basis of the ratio between the half value widths w1 and w2 from the following equation (Step 11).

$$L = f(w2/w1) \quad (6)$$

wherein f is a function to be experimentally determined.

The peak heights h1 and h2 and the half value width w1 are corrected on the basis of the depth L by the following equation for determination of corrected values H1, H2 and W (Step 12).

$$H1 = g1(h1, L) \quad (7)$$

$$H2 = g2(h2, L) \quad (8)$$

$$W = g3(w1, L) \quad (9)$$

wherein g1, g2 and g3 are functions to be experimentally determined.

The hemoglobin concentration HGB and the hematocrit HCT are computed in the aforesaid manner on the basis of the corrected values H1, H2 and W (Step 13).

In the analyzing section 2, the extracting section 21 implements Steps 2, 3, 7 and 8, the quantifying section 22 implements Step 4, 5, 9 and 10, and the computing section 23 implements Steps 11 to 14.

Figure 9:
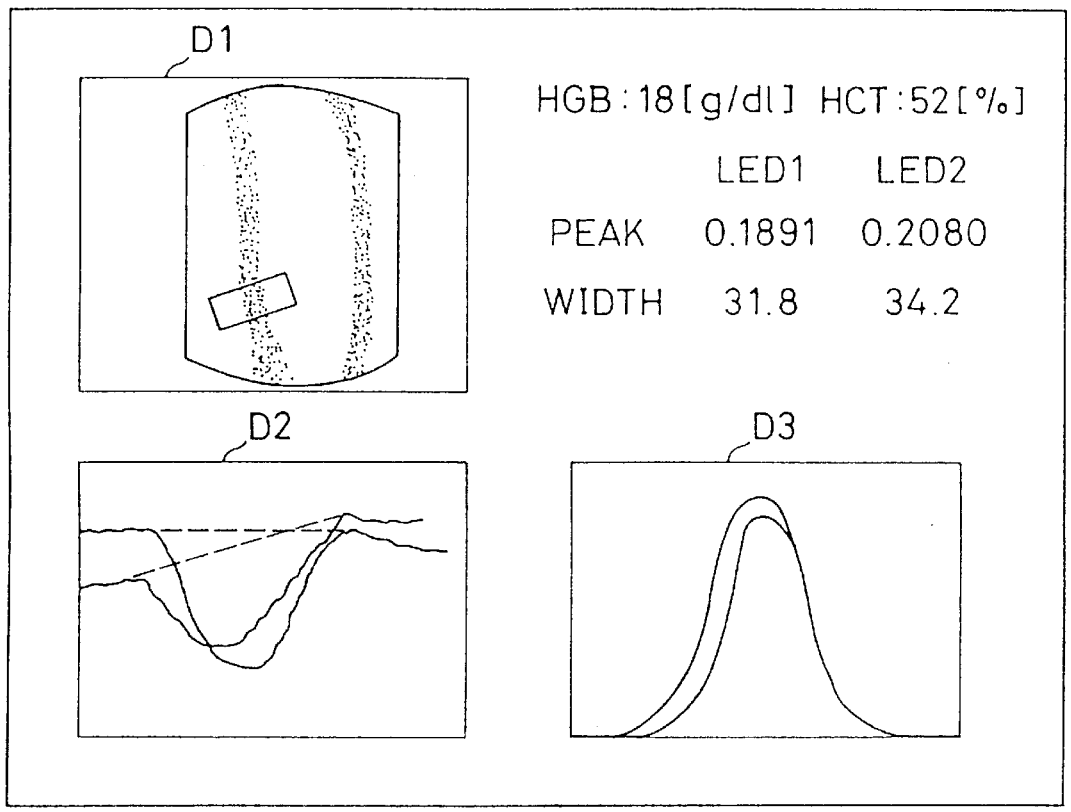
FIG. 9 is a diagram for explaining an exemplary display of the blood analyzer of Embodiment 1 of the present invention.

The results thus obtained are displayed in the outputting section (CRT) 24 as shown in FIG. 9.

In FIG. 9, images D1, D2 and D3 correspond to FIGS. 5, 6 and 7, respectively. "LED1" and "LED2" correspond to the LED 11a and LED 11b, respectively. "PEAK" and "WIDTH" correspond to the peak heights h1, h2 and the half value widths w1, w2, respectively.

Although the image pickup device 15 is comprised of the CCD in this embodiment, a line sensor may be employed instead. In such a case, the density profiles can directly be obtained in Steps 3 and 8 shown in FIG. 4. However, a special consideration is required, e.g., a line sensor having two line elements should be employed, because the line sensor is not always disposed perpendicular to the blood vessel.

While the computation of the hemoglobin concentration and the hematocrit has been described above, the analyzer according to this embodiment can also be used as an anemia checker. Since the hemoglobin concentration and the hematocrit are correlated with each other, the rough check of the degree of the anemia (anemia check) can be performed by implementing part of the process sequence (Steps 1 to 5) in FIG. 4 by using either one of the first and second wavelengths.

Further, where a blood vessel at a constant depth is of interest, the step for the depth correction can be omitted. Rough depth correction can be achieved by searching for an image area having the sharpest contrast as in Step 1a of FIG. 4.

Embodiment 2

There will first be described the construction of a blood analyzer according to Embodiment 2 of the present invention.

In this embodiment, the image pickup section 12 and the analyzing section 2 are modified for more precise correction than the correction process in Embodiment 1.

Figure 10:
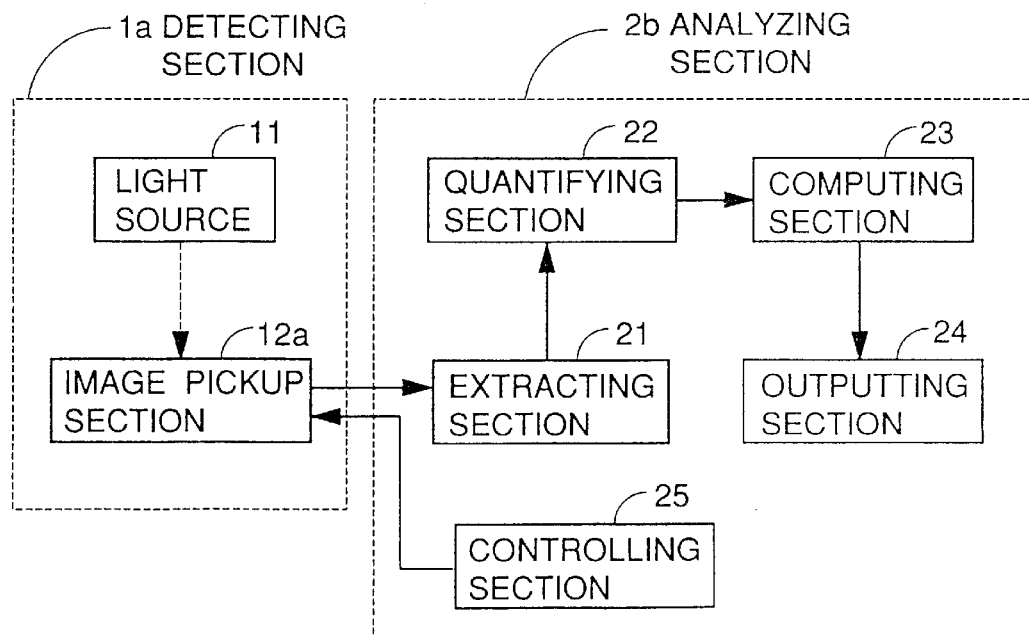
FIG. 10 is a block diagram illustrating the construction of a blood analyzer according to Embodiment 2 of the present invention.

FIG. 10 is a block diagram illustrating the construction of the analyzer of Embodiment 2, in which like reference numerals denote like parts in FIG. 1. A detecting section 1a includes a light source 11 for illuminating part of tissues of a living body including a blood vessel, and an image pickup section 12a having a conjugate optical system.

Figure 11:
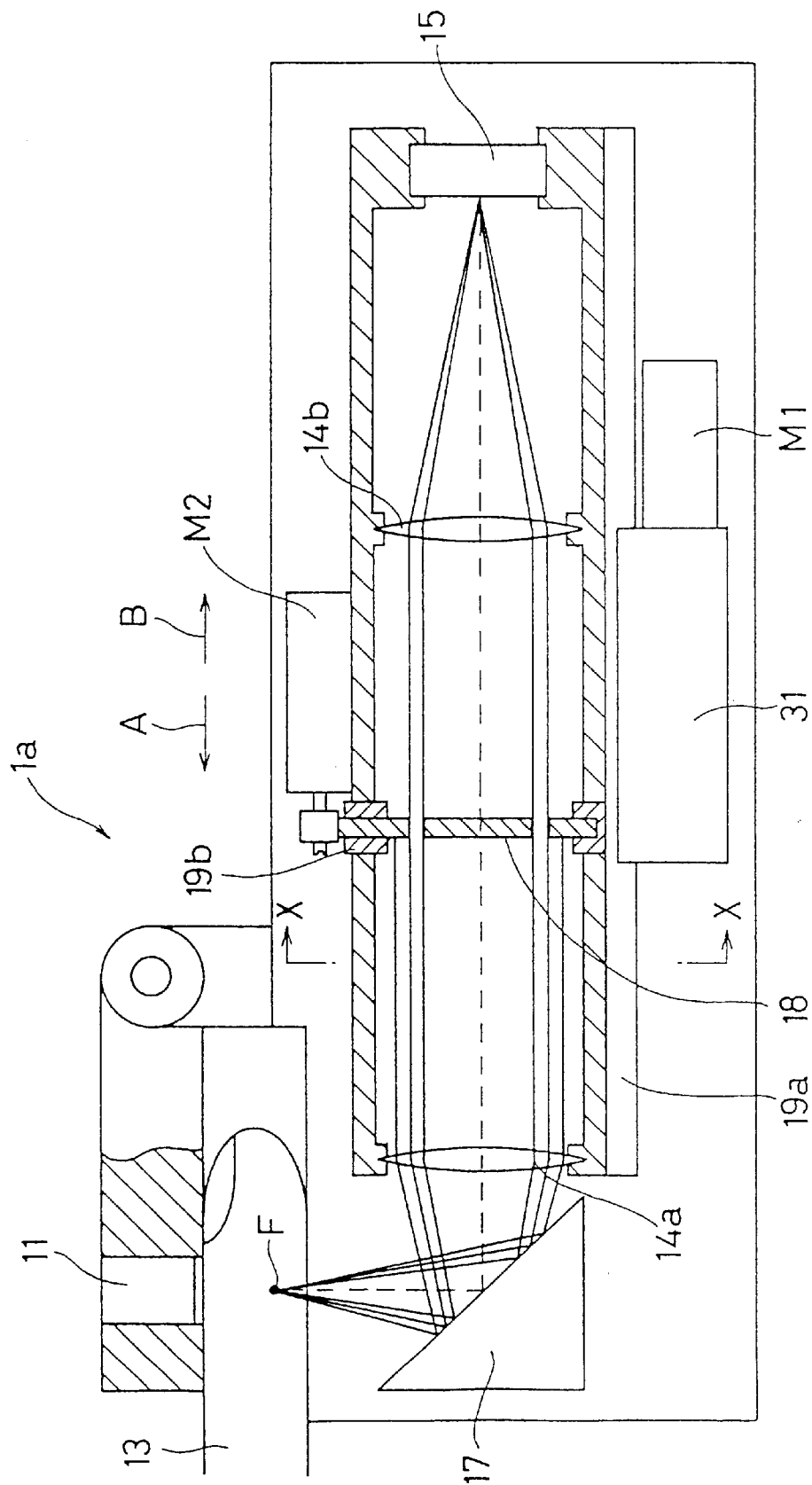
FIG. 11 is a sectional view illustrating major portions of the blood analyzer of Embodiment 2 of the present invention.

FIG. 11 is a sectional view of the detecting section 1a. The light source 11 has the same construction as in Embodiment 1 and, therefore, an explanation thereto is omitted.

The image pickup section 12a includes a driving stage 19a movable in directions of arrows A and B and incorporating an object lens 14a and a focusing lens 14b each having the same numerical aperture, an image pickup device 15, a space filter 18 and a filter driving section 19b, and a mirror 17.

The rear focal point of the lens 14a coincides with the front focal point of the lens 14b. That is, the lenses 14a and 14b are disposed so as to have a common focal point, at which the space filter 18 is disposed. The image pickup device 15 is disposed at the rear focal point of the lens 14b. Like in Embodiment 1, a CCD or the like is employed as the image pickup device 15.

As shown in FIG. 11, the stage 19a is mounted on a sliding mechanism 31, which is moved in the directions of the arrows A and B by driving a stepping motor M1 to be. Thus, the position of the focal point F of the lens 14a can be adjusted.

Figure 12:
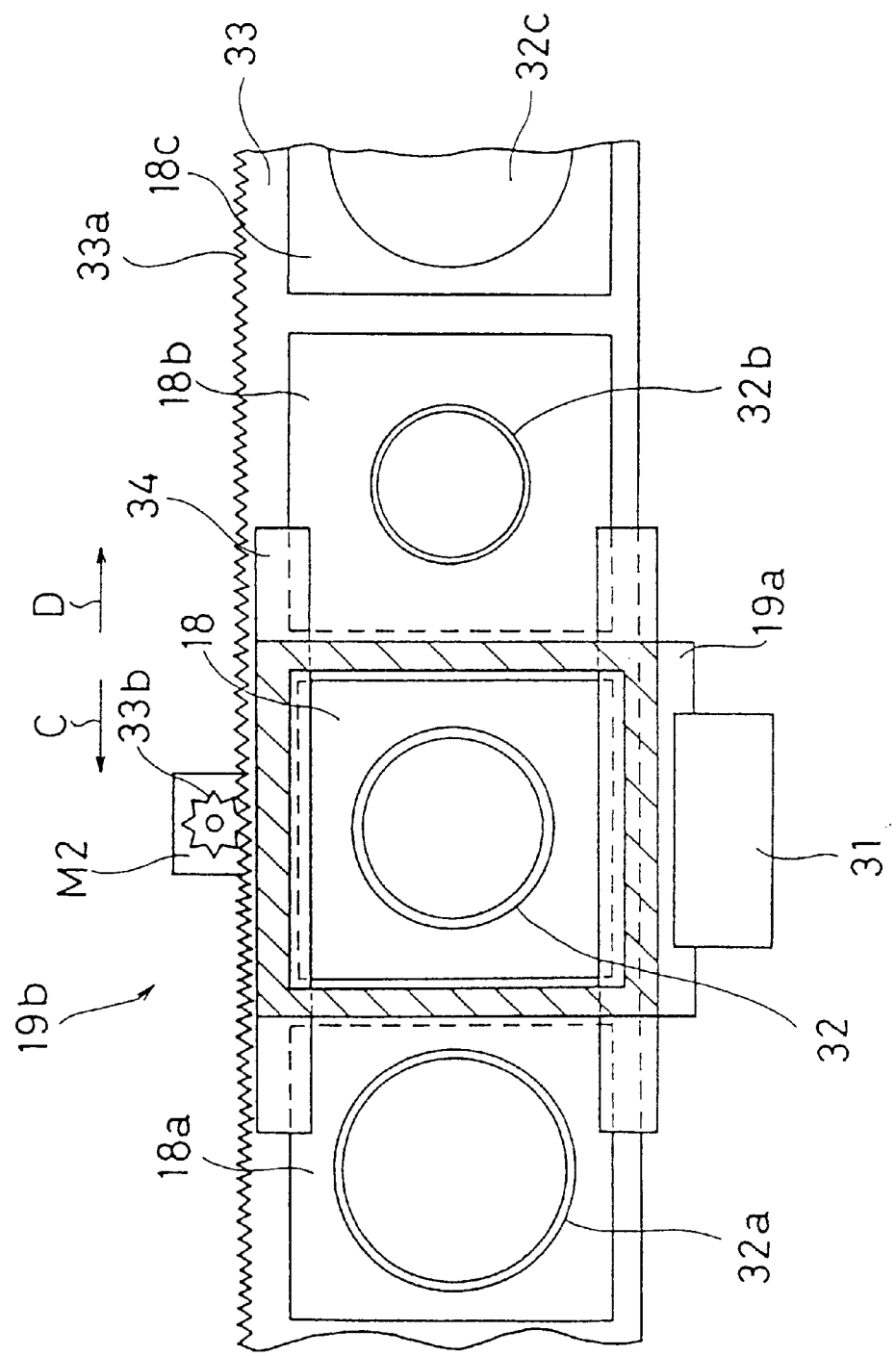
FIG. 12 is a sectional view taken along a line X—X in FIG. 11.

FIG. 12 is a sectional view taken along a line X—X in FIG. 11. The filter driving section 19b has a sliding section 34 which supports a filter attachment plate 33 slidably in directions of arrows C and D. Since a pinion 33b of the stepping motor M2 engages a rack 33 provided in the upper portion of the filter attachment plate 33, the filter attachment plate 33 travels in the directions of the arrows C and D when the stepping motor M2 is driven.

Space filters 18, 18a, 18b and 18c are attached to the filter attachment plate 33. The space filters 18, 18a and 18b are light blocking plates respectively including annular light transmission slits 32, 32a and 32b having different diameters. The space filter 18c is a light blocking plate having a round light transmission window 32c.

Therefore, any selected one of the space filters 18, 18a, 18b and 18c can be placed at the common focal point by means of the filter driving section 19b. A situation where virtually no filter is placed can be created by placing the space filter 18c at the common focal point.

The analyzing section 2b includes an extracting section 21 for extracting a profile from the picked image, a quantifying section 22 for quantifying the profile, a computing section 23 for computing the hemoglobin concentration and the hematocrit on the basis of parameters thus quantified, an outputting section (CRT) 24 for displaying computation results, and a controlling section 25 for driving the stepping motors M1 and M2 to control the position of the focal point and the insertion of the space filters.

In the detecting section 1a, as shown in FIG. 11, light emitted from the light source 11 is allowed to pass through a finger 16, then turned by 90β by means of the mirror 17, and focused on the image pickup device 15 via the lenses 14a and 14b.

Where the space filter 18 (FIG. 12) is located at the position of the common focal point, only light scattered at a particular angle by tissues of the finger 13 is focused on the image pickup device 15. The particular angle is determined by the diameter of the slit 32.

Further, by moving the stage 19a along the optical axis (in the direction of the arrow A or B), the focal point F can be located at a desired position in the tissues of the finger 16.

Figure 13:
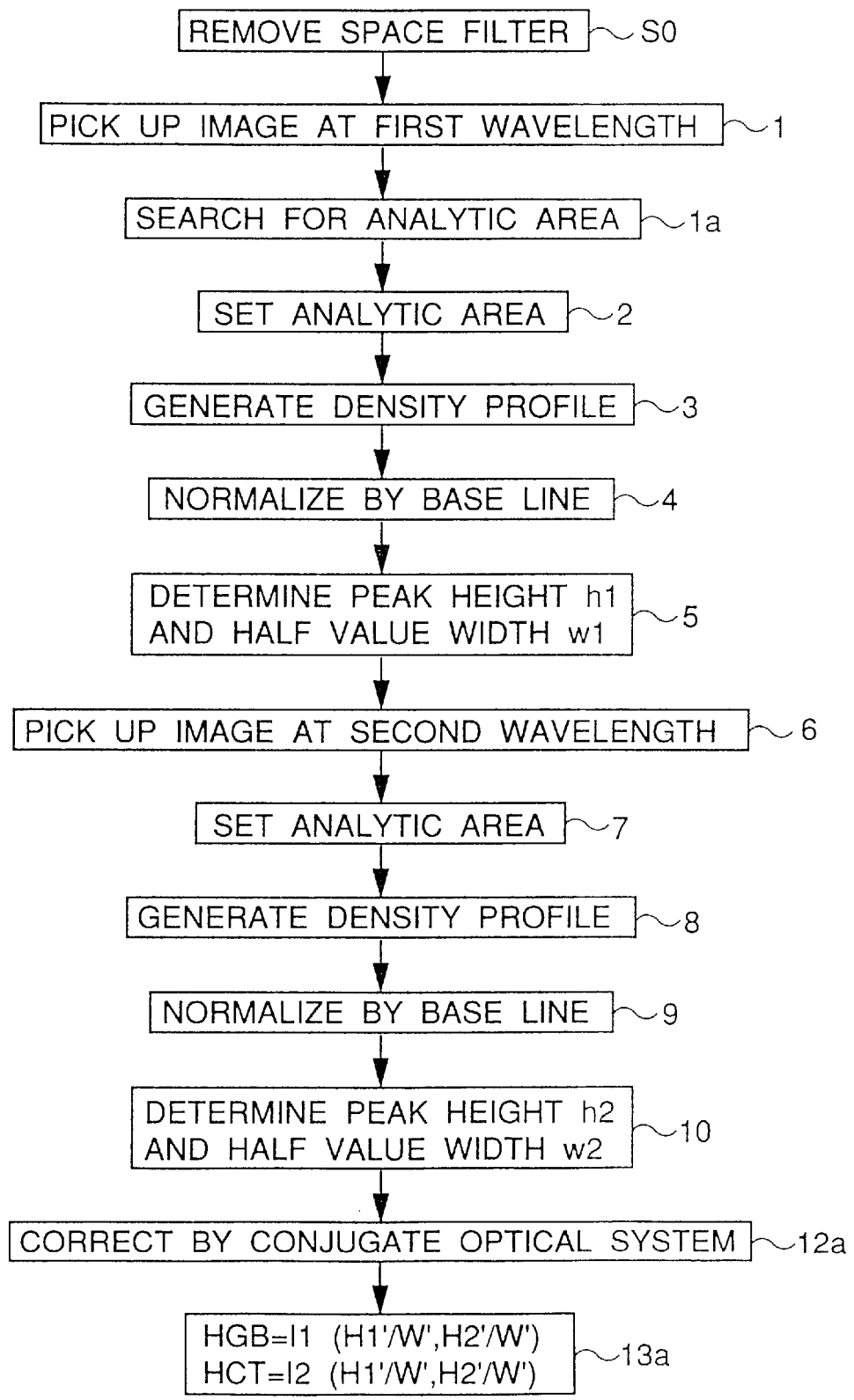
FIG. 13 is a flow chart illustrating the operation of the blood analyzer of Embodiment 2 of the present invention.

An analyzing process to be performed by the analyzing section 2b of the blood analyzer having such a construction will be described with reference to a flow chart shown in FIG. 13.

(1) Computation of Hemoglobin Concentration and Hematocrit

First, the space filter 18 is removed from the position of the common focal point by the filter driving means 19b (Step S0). Thus, the image pickup section has substantially the same construction as the image pickup section in Embodiment 1. Since the process for computing the hemoglobin concentration and the hematocrit which is performed in accordance with subsequent steps 1a to 10 is the same as in Embodiment 1 shown in FIG. 4, an explanation thereto is omitted.

(2) Correction of Computed Hemoglobin Concentration and Hematocrit

Figure 14:
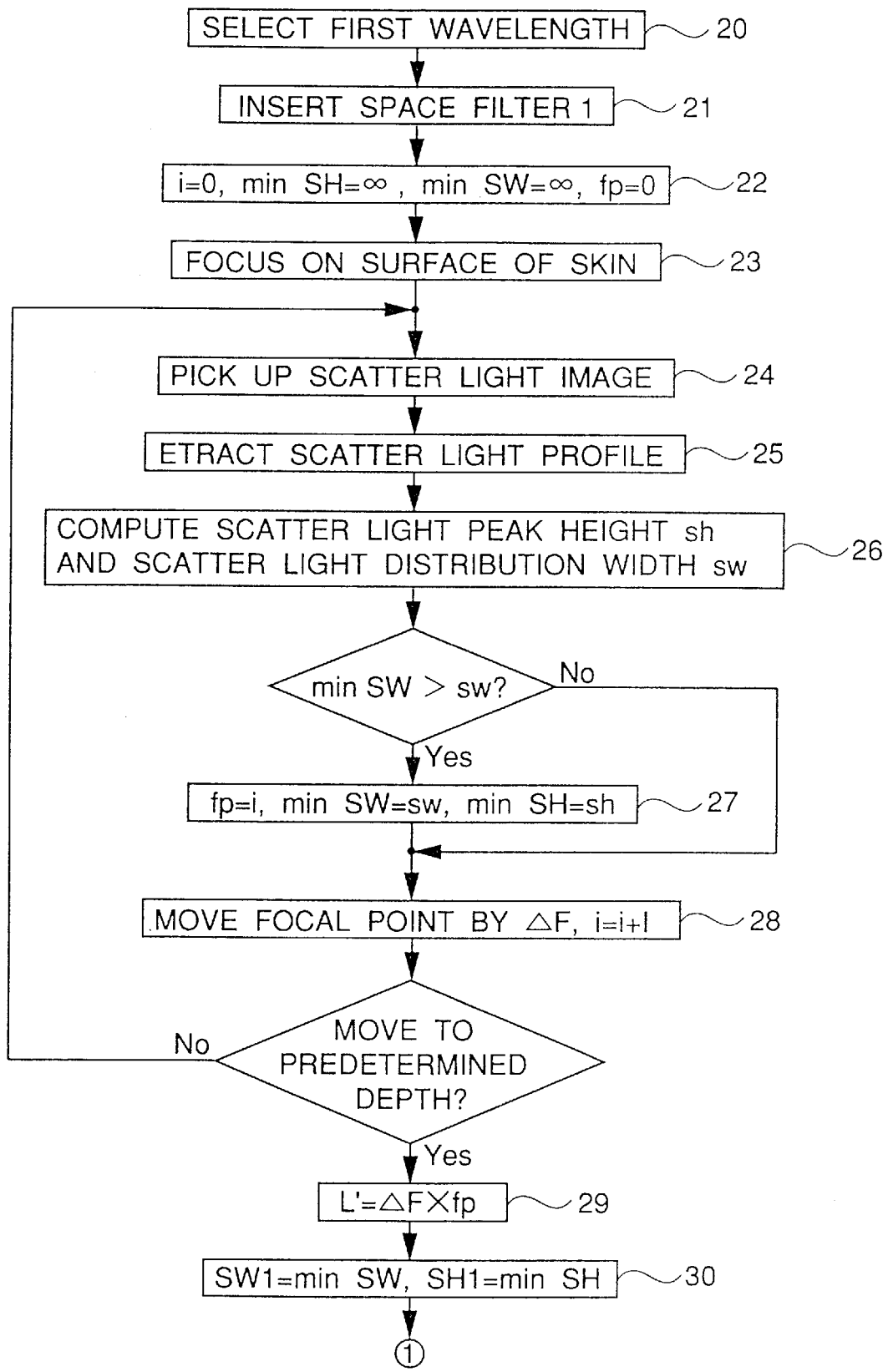
FIG. 14 is a flow chart illustrating the operation of the blood analyzer of Embodiment 2 of the present invention.
Figure 15:
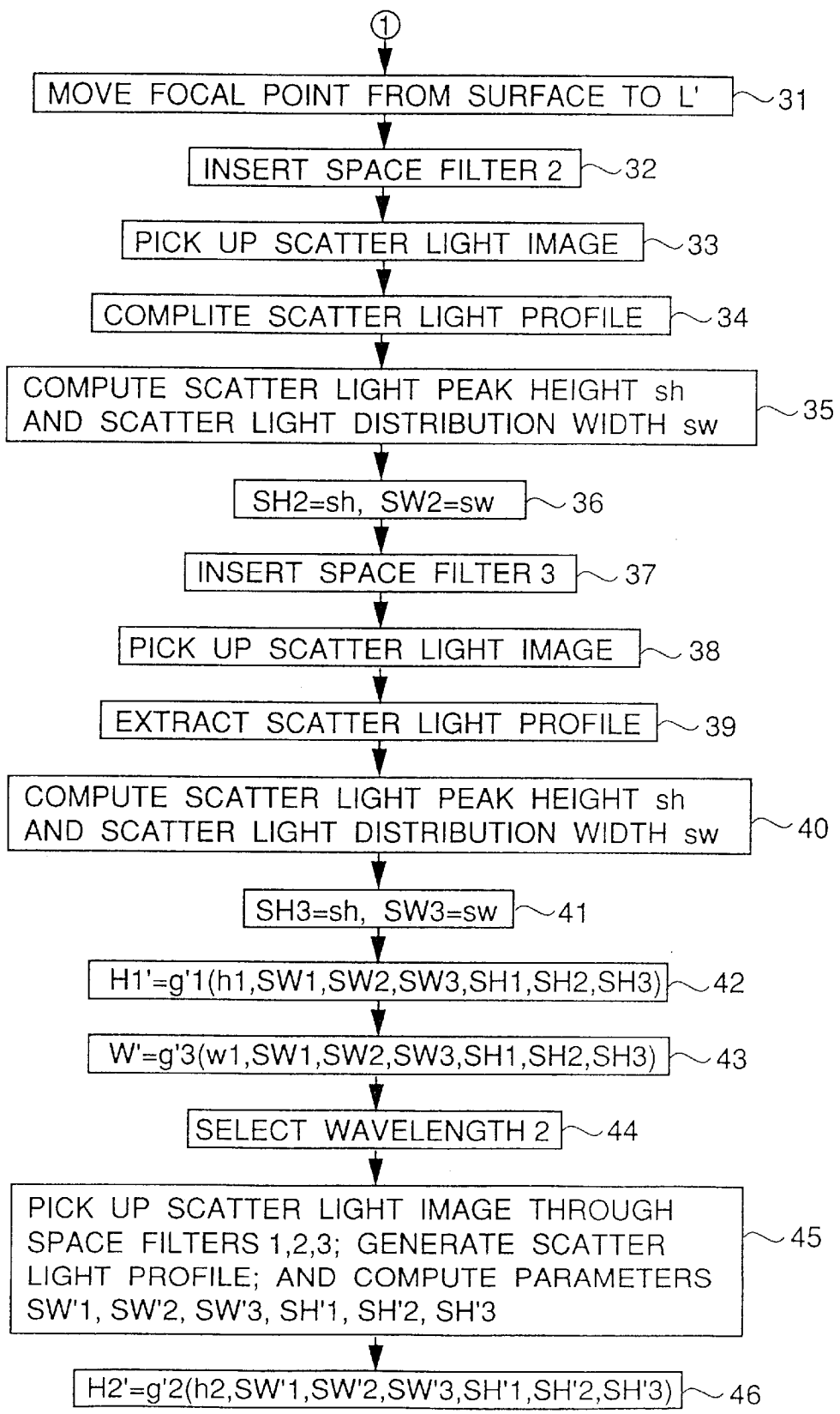
FIG. 15 is a flow chart illustrating the operation of the blood analyzer of Embodiment 2 of the present invention.

Since this embodiment is characterized by a correction process in Step 12a, the correction process will hereinafter be described in greater detail with reference to flow charts shown in FIGS. 14 and 15.

The space filter 18 is set at the position of the common focal point by means of the filter driving section 19b (Step 21).

In this state, the focal point F is located on the skin surface of the finger (Step 23). The initial position of the focal point F is predetermined because the finger insertion position is preliminarily fixed.

Then, an image is picked up (Step 24).

Figure 4:
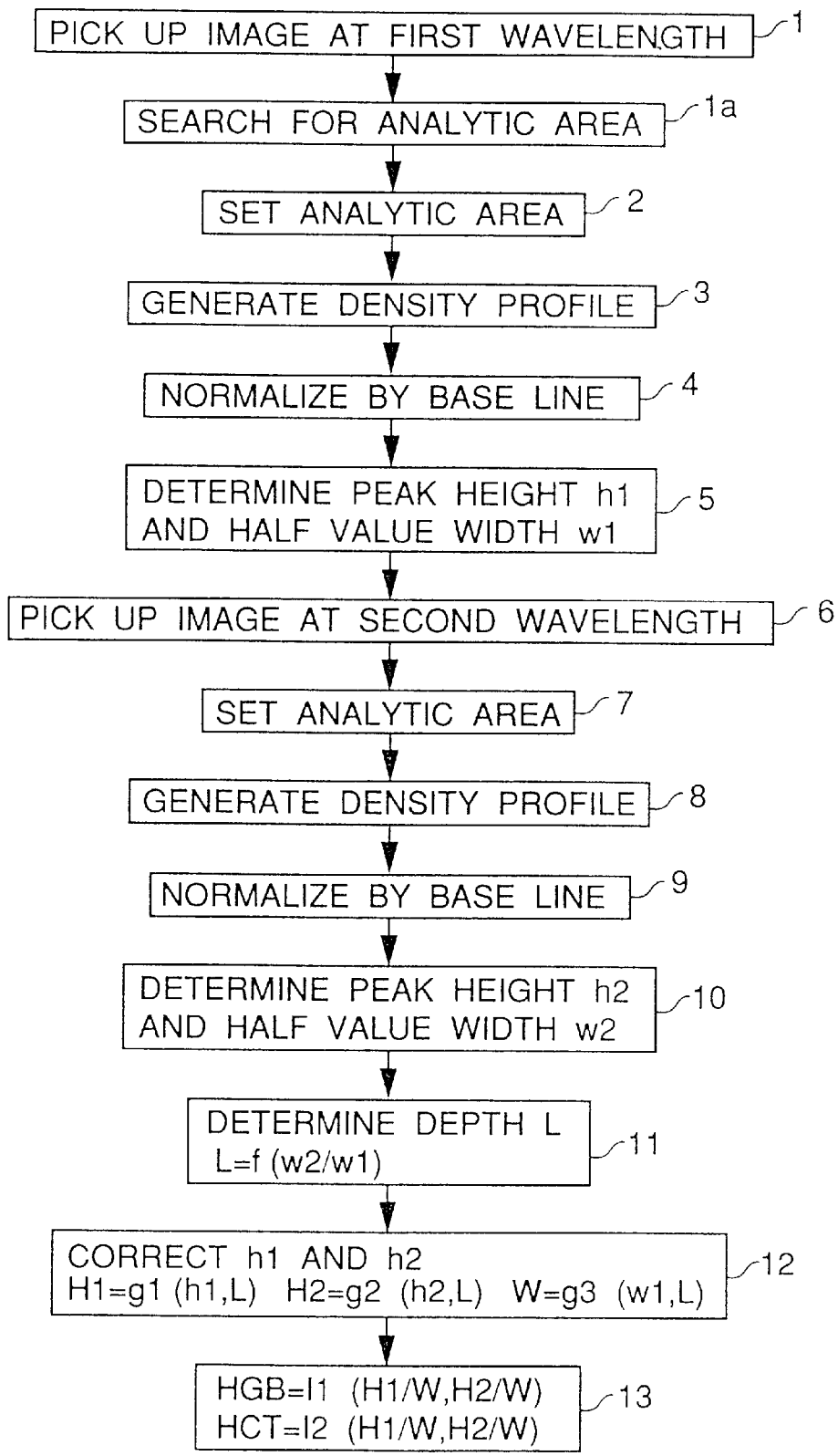
FIG. 4 is a flow chart for explaining the operation of the blood analyzer of Embodiment 1 of the present invention.

The image pickup step is different from Step 1 (FIG. 4). That is, the picked image is formed from light scattered within that particular angle, and hereinafter referred to as "scatter image" for avoidance of confusion.

Figure 16:
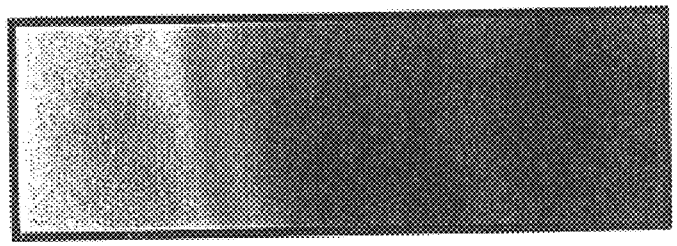
FIG. 16 is a photograph of an image (a gray scale image displayed on a CRT) picked by the blood analyzer of Embodiment 2 of the present invention.
Figure 20:
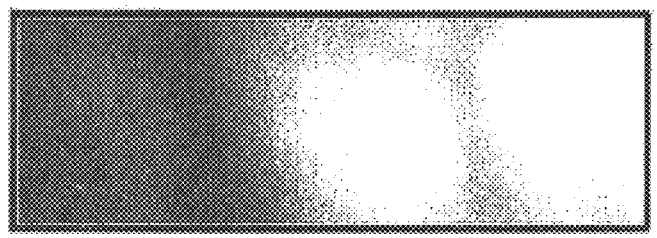
FIG. 20 is a photograph illustrating a comparative example with respect to FIG. 16.

The scatter image is shown in FIG. 16. It should be noted that, since the scatter image is formed from the scatter light alone, only peripheral portions of the blood vessel in the scatter image have a high brightness. For reference, an image of the same object obtained in Step 1 of FIG. 4 is shown in FIG. 20.

Figure 17:
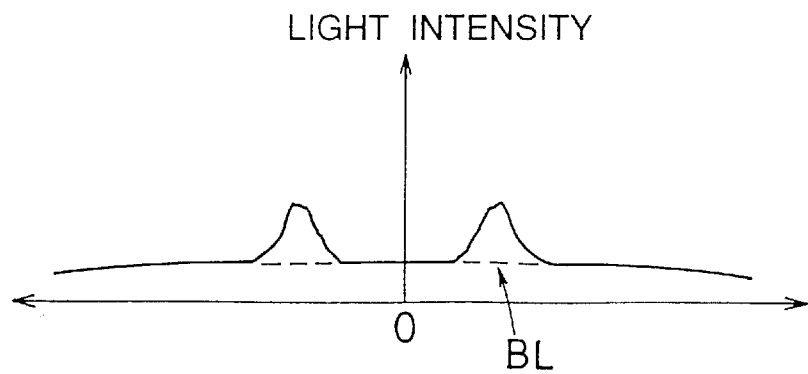
FIG. 17 is a graphical representation for explaining an image density profile obtained by the blood analyzer of Embodiment 2 of the present invention.

In the extracting section 21, a profile within the analytic area defined in Step 2 (FIG. 4) is obtained from the scatter image (Step 25). This profile is referred to as "scatter profile" for discrimination thereof from the image density profile obtained in Step 3 (FIG. 4). An exemplary scatter profile is shown in FIG. 17.

Figure 18:
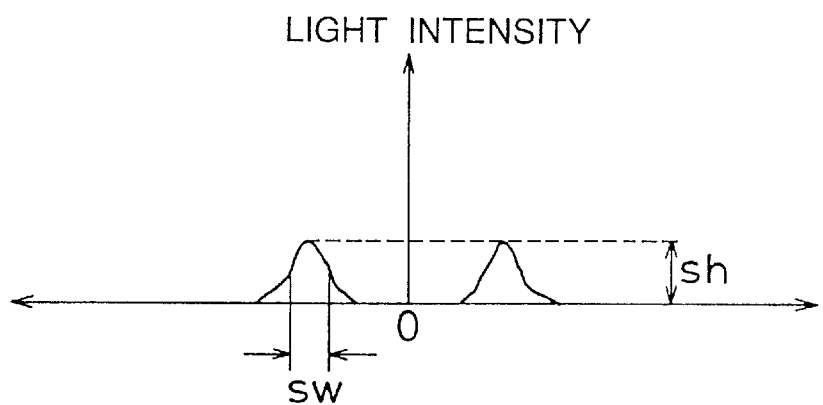
FIG. 18 is a graphical representation for explaining an image density profile normalized in the blood analyzer of Embodiment 2 of the present invention.

Further, the quantifying section 22 determines a base line BL of the scatter profile, and then a peak height sh and a distribution width sw of the scatter profile are determined as shown in FIG. 18 (Step 26).

The peak height and the distribution width will hereinafter be referred to as "scatter peak height SH" and "scatter distribution width SW", respectively, for avoidance of confusion. A value of the scatter distribution width SW thus determined is once stored as the minimum value (Step 27).

In turn, the focal point F is moved by a predetermined distance ΔF inwardly of the finger 13 (Step 28).

The distance ΔF is of the order of 0.1 mm.

In this state, the process sequence of Steps 24 to 26 is repeated for determination of the scatter peak height sh and the scatter distribution width sw.

The scatter distribution width sw thus determined is compared with the minimum value previously stored. If the scatter distribution width sw is smaller than the stored value, the scatter distribution width is employed as a new minimum value (Step 27).

The process sequence of Steps 24 to 27 is repeated until the focal point reaches a predetermined depth (Step 28).

The predetermined depth may be about 2 mm, since the blood vessel of interest is typically located at a subcutaneous depth of 1 to 2 mm.

Figure 19:
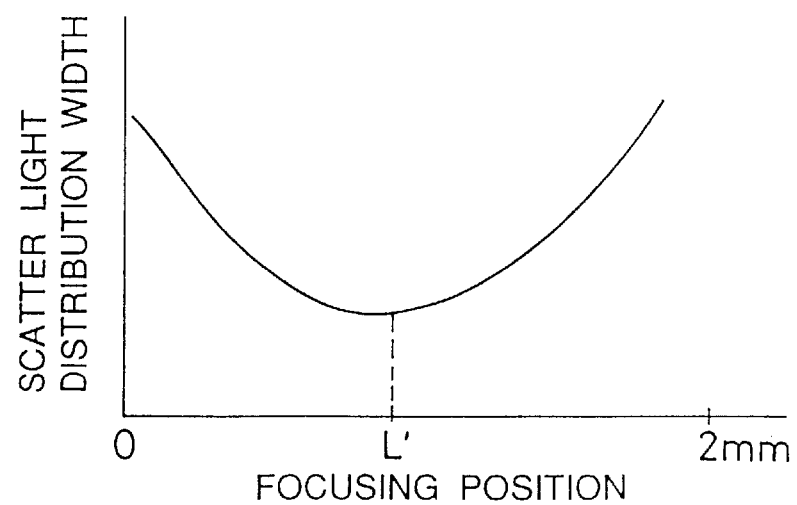
FIG. 19 is a graphical representation for explaining the position of a focal point and the width of scatter distribution detected by the blood analyzer of Embodiment 2 of the present invention.

The scatter peak widths SW thus obtained are plotted with respect to the position of the focal point as shown in FIG. 19. The scatter peak width is the minimum when the focal point is located at the depth at which the blood vessel is present. This means that, when the focal point of the image pickup system coincides with the position of the blood vessel of interest, the scatter light image is the sharpest.

Therefore, the position of the focal point which AAA offers a blood vessel image having the minimum width corresponds to the subcutaneous depth L' of the blood vessel described in Embodiment 1 (Step 29). That is, the subcutaneous depth can be determined more accurately. A scatter peak height SH1 and a scatter distribution width SW1 are obtained in this state (Step 30).

In accordance with this flow chart, only the minimum value of the scatter distribution width is stored. Alternatively, all the scatter peak heights SH and scatter distribution width SW obtained by changing the position of the focal point are stored, and then fitted to an appropriate function for determination of the minimum value.

In turn, the focal point of the image pickup system is moved to the subcutaneous depth L' (Step 31), and then the space filter currently employed is replaced with the space filter 18a is attached by means of the filter driving section 19b.

The space filter 18a is different in the diameter from the space filter 18. This means that the angle range of the scatter light for the image formation is changed.

A scatter light image is picked up with the use of the space filter 18a (Step 33), and the extraction (Step 34) and quantification (Step 35) of a scatter profile are carried out in the same manner as described above. Then, a scatter peak height SH2 and a scatter distribution width SW2 are determined (Step 36). Further, substantially the same process sequence as described above is performed with the use of the space filter 18b (steps 37 to 41).

The scatter peak heights SH1 to SH3 and the scatter distribution widths SW1 to SW3 thus obtained reflect the optical characteristics, i.e., the scatter factor and absorption factor of the tissues of the living body. More specifically, the scatter peak height decreases, as the absorption factor of the living body becomes higher. The scatter peak height decreases and the scatter distribution width increases, as the scatter factor becomes higher. Therefore, these parameters reflect the scatter factor and absorption factor of the tissues of the living body.

As described in Embodiment 1, the image density profile is influenced by the disturbance by the body tissues. The correction for the disturbance is carried out on the basis of the ratio between the distribution widths of the image density profiles in Embodiment 1.

In Embodiment 2, since the disturbance by the body tissues can directly be quantified on the basis of the aforesaid parameters, more accurate results can be obtained. More specifically, the peak height h1 and the distribution width w1 in the equation (4) are corrected by the following equation for determination of a corrected peak height H1 and a corrected distribution width W (Steps 42 and 43).

$$H1'=g1'(h1,L', SH1, SH2,SH3,SW1,SW2,SW3) \qquad (10)$$

$$W'=g3'(w1,L'SH1,SH2,SH3,SW1,SW2,SW3) \qquad (11)$$

Functions g1' and g3' may be experimentally determined or, alternatively, may be theoretically determined.

For measurement at the second wavelength (Step 44), the replacement of the space filter, the pickup of a scatter image, the extraction of a scatter profile, the computation of scatter parameters SH1' to SH3' and SW1' to SW2' are carried out (Step 45), and then the peak height h2 in the equation (4) is corrected as follows for determination of a corrected peak height H2' (Steps 44 and 45).

$$H2'=g2'(h2,L',SH1',SH1',SH2',SH3',SW1',SW2',SW3') \qquad (12)$$

A function g2' is determined in the same manner as the function g1'. Then, the routine returns to Step 13a in FIG. 13. The hemoglobin concentration HGB and the hematocrit HCT are determined on the basis of H1', H2' and W' (Step 13a).

Embodiment 3

The blood analyzers described in Embodiments 1 and 2 are a blood analyzer of transmitted light type in which the concentration of a blood constituent is computed on the basis of a transmitted light image. On the other hand, Embodiment 3 employs a blood analyzer of reflected light type in which the concentration of a blood constituent is computed on the basis of a reflected light image.

While the measurement site for the blood analyzer of transmitted light type is limited to fingers and earlobes through which the light can be transmitted, the blood analyzer of reflected light type is advantageous in that it can be applied to a wide range of bodily portions such as a sole, a cheek, and an abdomen. Therefore, the blood analyzer of reflected light type is effective on subjects such as an infant and a baby whose fingers cannot be easily fixed and held.

Also, a reflected light employed in this Embodiment can be in a shorter wavelength range, namely, 400 nm to 950 nm. Since the light having a shorter wavelength is absorbed by hemoglobin to a greater extent, it is possible to perform a more accurate measurement.

Figure 21:
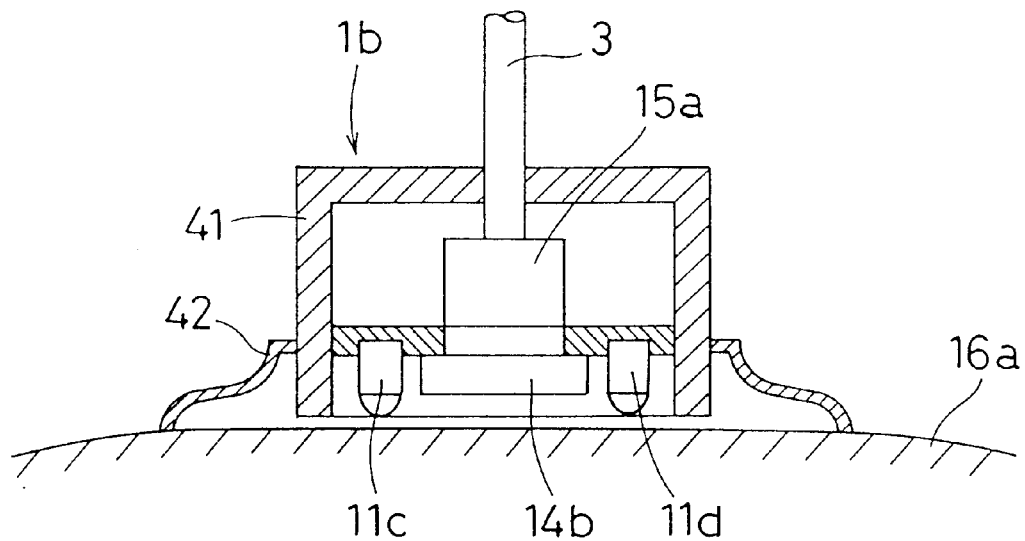
FIG. 21 is a sectional view showing a structure of a detecting section according to Embodiment 3 of the present invention.
Figure 22:
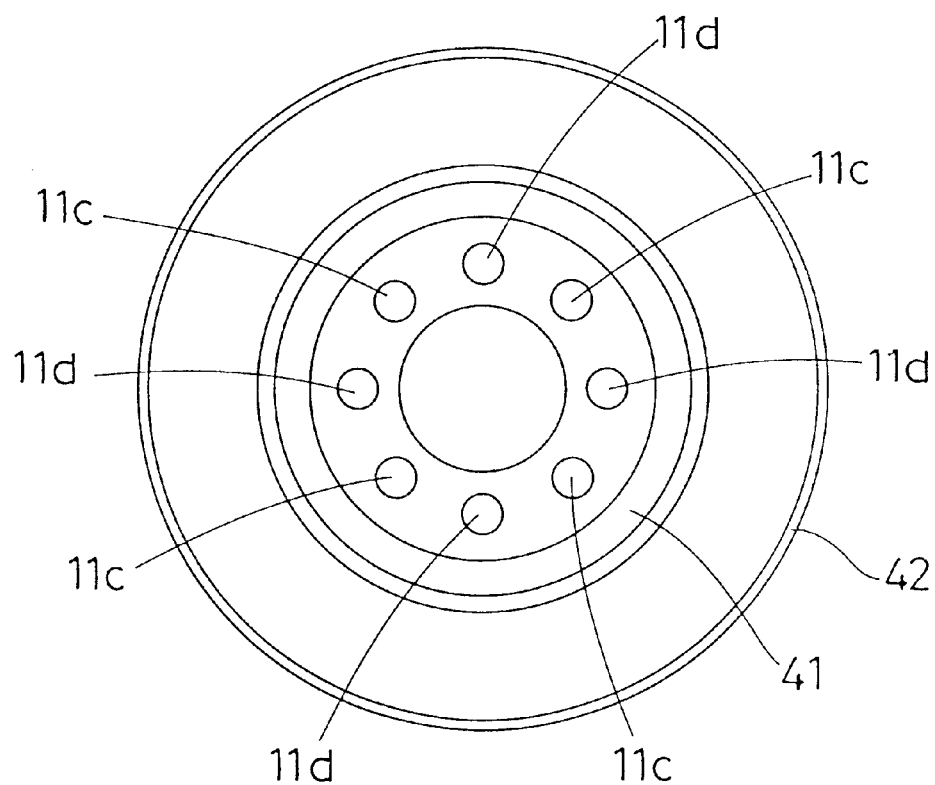
FIG. 22 is a bottom view of the detecting section.

There will next be described the construction of the blood analyzer according to Embodiment 3 of the present invention. FIG. 21 is a sectional view showing a structure of a detecting section 1b according to Embodiment 3 of the present invention. FIG. 22 is a bottom view of the detecting section 1b. Here, the blood analyzer of Embodiment 3 is the same as the blood analyzer of Embodiment 1 except that the detecting section is modified and, therefore, an explanation of the other elements is omitted.

As shown in FIGS. 21 and 22, the detection section 1b is compactly constructed by incorporating an image pickup device 15a and a lens 14b disposed in a central portion of a tubular housing 41, and by disposing LEDs 11c and 11d in the periphery thereof as a light source. The light source may include laser diodes or may be introduced from outside by employing a ring fiber. If a larger quantity of light is required in the blood analyzer of reflected light type than in the blood analyzer of transmitted light type, the number of the light sources, i.e., LEDs 11c and 11d can be increased to meet the requirement in this Embodiment.

A bell-like rubber seat 42 is provided in the periphery of the housing 41 for stably holding the detecting section 1b on a bodily portion 16a. Here, the LEDs 11c and 11d emit lights of different wavelengths, which correspond to the first and second wavelengths in Embodiment 1. Images obtained from the detecting section 1b are processed in the manner already explained in Embodiment 1.

INDUSTRIAL APPLICABILITY

The industrial applicability of the present invention is as follows:

(1) A transcutaneous blood analysis can be realized without employing the avascularization method or the sphygmic spectrometry;

(2) A transcutaneous and noninvasive determination of the hemoglobin concentration and the hematocrit can be realized with a simple construction;

(3) Since a particular measuring object (a particular blood vessel of interest) can be defined, results can be obtained with an improved reproducibility;

(4) The hemoglobin concentration and the hematocrit can continuously be monitored;

(5) Results can be obtained with an improved reproducibility by way of image processing;

(6) A blood analyzer having a reduced size can be realized at a low cost; and (7) The blood analyzer can be used as an anemia checker.

What is claimed is:

1. A noninvasive blood analyzer comprising:
    a light source for illuminating part of a tissue of a living body including a blood vessel;
    an image pickup section for picking up an image of the illuminated blood vessel and tissue; and
    an analyzing section for analyzing the image, wherein the analyzing section includes;
    an extracting section for extracting an image density distribution across the blood vessel in the image as an image density profile;
    a quantifying section for quantifying configurational characteristics of the image density profile;
    a computing section for computing an amount of a blood constituent on the basis of the quantified characteristics; and
    an outputting section for outputting the computed amount.

2. A noninvasive blood analyzer as set forth in claim 1, wherein the amount of the blood constituent is at least one of hemoglobin concentration and hematocrit.

3. A noninvasive blood analyzer as set forth in claim 2, wherein the image pickup section includes an object lens, a focusing lens, a space filter disposed between the lenses and having two-dimensionally variable transmittances, and filter controlling means for two-dimensionally varying the transmittance of the space filter.

4. A noninvasive blood analyzer as set forth in claim 3, wherein the image pickup section further includes adjusting means for adjusting the position of a focal point of the object lens with respect to the blood vessel.

5. A noninvasive blood analyzer as set forth in claim 4, wherein the quantifying section normalizes the image density profile, and computes a peak value h and a distribution width w corresponding to the diameter of the blood vessel from the normalized image density profile.

6. A noninvasive blood analyzer as set forth in claim 5, wherein the quantifying section computes a depth L defined between a surface of the body tissues and the blood vessel on the basis of the position of the focal point of the object lens which is adjusted by the adjusting means such that the sharpest image is picked up, and corrects the peak value h and the distribution width w on the basis of the depth L.

7. A noninvasive blood analyzer as set forth in claim 3, wherein the quantifying section normalizes the image density profile, and computes a peak value h and a distribution width w corresponding to the diameter of the blood vessel from the normalized image density profile.

8. A noninvasive blood analyzer as set forth in claim 7, wherein the quantifying section corrects the peak value h and the distribution width w on the basis of a plurality of images picked up every time the transmittance of the space filter is two-dimensionally varied.

9. A noninvasive blood analyzer as set forth in claim 1, wherein the light source comprises a light emitting device which is adapted to selectively emit light beams of first and second wavelengths, which are substantially isosbestic for oxidized and reduced hemoglobins.

10. A noninvasive blood analyzer as set forth in claim 1, wherein the extracting section searches for an area in the image where a blood vessel image stands in the sharpest contrast and extracts the image density profile from the area thus searched for.

11. A noninvasive blood analyzer as set forth in claim 1, wherein the quantifying section normalizes the image density profile, and computes a peak value h and a distribution width w corresponding to the diameter of the blood vessel from the normalized image density profile.

12. A noninvasive blood analyzer as set forth in claim 11,
    wherein the light source comprises a light emitting device which is adapted to selectively emit light beams of first and second wavelengths;
    wherein the quantifying section computes peak values h1 and h2 and distribution widths w1 and w2 of first and second profiles respectively obtained by picking up images of the same part of the body tissues at the first and second wavelengths; and
    wherein the computing section computes the concentration of hemoglobin and hematocrit on the basis of the computed peak values h1 and h2 and distribution widths w1 and w2.

13. A noninvasive blood analyzer as set forth in claim 12, wherein the quantifying section estimates a depth L at which the blood vessel is located on the basis of the distribution widths w1 and w2 of the first and second image density profiles obtained by picking up images of the same part of the body tissues at the first and second wavelengths, and corrects the peak values h1 and h2 on the basis of the depth L.

14. A noninvasive blood analyzer as set forth in claim 1, further comprising a fixing member for relatively fixing the living body to the light source and the image pickup section.

15. A noninvasive blood analyzer as set forth in claim 1, wherein the image pick up section picks up a transmitted light image of the blood vessel and the tissue.

16. A noninvasive blood analyzer as set forth in claim 1, wherein the image pick up section picks up a reflected light image of the blood vessel and the tissue.

17. A noninvasive blood analyzer comprising:
    a light source for illuminating part of a tissue of a living body including a blood vessel;
    an image pickup section for picking up an image of the illuminated blood vessel and the tissue; and
    an analyzing section for analyzing the image, the analyzing section analyzing an image of the blood vessel in the image to compute an amount of a blood constituent and output a computation result;
    wherein the light source comprises a light emitting device which is adapted to selectively emit light beams of first and second wavelengths, which are within a range between 600 and 950 nm.

18. A noninvasive blood analyzer as set forth in claim 17, wherein the amount of the blood constituent is at least one of hemoglobin concentration and hematocrit.

19. A noninvasive blood analyzer as set forth in claim 17, further comprising a fixing member for relatively fixing the living body to the light source and the image pickup section.

20. A noninvasive blood analyzer as set forth in claim 17, wherein the image pickup section-picks up a transmitted light image of the blood vessel and the tissue.

21. A noninvasive blood analyzer as set forth in claim 17, wherein the image pickup section picks up a reflected light image of the blood vessel and the tissue.

22. A noninvasive blood analyzer comprising:
- a light source for illuminating part of a tissue of a living body including a blood vessel;
- an image pickup section for picking up an image of the illuminated blood vessel and the tissue; and
- an analyzing section for analyzing the image, the analyzing section analyzing an image of the blood vessel in the image to compute an amount of a blood constituent and output a computation result;

wherein the image pickup section includes an object lens, a focusing lens, a space filter disposed between the lenses and having two-dimensionally variable transmittances, and filter controlling means for two-dimensionally varying the transmittance of the space filter.

23. A noninvasive blood analyzer as set forth in claim 22, wherein the image pickup section further includes adjusting means for adjusting the position of a focal point of the object lens with respect to the blood vessel.

* * * * *